United States Patent [19]

Hart et al.

[11] Patent Number: 5,064,843
[45] Date of Patent: Nov. 12, 1991

[54] PYRID-3-YL THIOFORMAMIDE COMPOUNDS WHICH HAVE USEFUL PHARMACEUTICAL UTILITIES

[75] Inventors: Terance W. Hart, Brentwood; Bernard Y. J. Vacher, Dagenham; Brian W. Sharp, Hornchurch, all of England

[73] Assignee: Rhone-Poulenc Sante, Antony, France

[21] Appl. No.: 501,888

[22] Filed: Mar. 30, 1990

[30] Foreign Application Priority Data

Mar. 31, 1989 [GB] United Kingdom ............... 8907306

[51] Int. Cl.$^5$ ............... A61K 31/16; C07D 239/26
[52] U.S. Cl. ....................... 514/346; 514/357; 546/300; 546/331
[58] Field of Search ............ 546/336, 331, 300; 514/357, 351, 346

[56] References Cited

U.S. PATENT DOCUMENTS 3,823,152  9/1974  Morimoto ............... 546/122
4,379,154  5/1983  Aloup et al. ............ 546/122

FOREIGN PATENT DOCUMENTS 321273   6/1989  European Pat. Off. ...... 546/122
0321274  6/1989  European Pat. Off. ...... 546/331
1351024  4/1974  United Kingdom ......... 546/122

OTHER PUBLICATIONS

European Search Report dated Jun. 15, 1990.

Primary Examiner—C. Warren Ivy
Assistant Examiner—Zinna Northington-Davis
Attorney, Agent, or Firm—Morgan & Finnegan

[57] ABSTRACT

This invention relates to a thioformamide derivative of the formula I

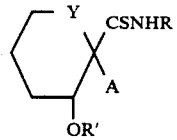

wherein:
R and $R^1$ each independently represent an alkyl group;
A represents either:
 (1) a phenyl group which is optionally substituted; or
 (2) a heteroaromatic group (e.g. pyrid-3-yl, quinolin-3-yl); and
Y represents:
 an ethylene or methylene group or a direct bond.

These compounds may be formulated as pharmaceutical preparations and have utility for the treatment of disorders associated with smooth muscle contraction.

7 Claims, No Drawings

PYRID-3-YL THIOFORMAMIDE COMPOUNDS WHICH HAVE USEFUL PHARMACEUTICAL UTILITIES

FIELD OF THE INVENTION

This invention relates to new therapeutically useful thioformamide derivatives, to processes for their preparation and to pharmaceutical compositions containing them

DESCRIPTION OF THE INVENTION

The new thioformamide derivatives of the present invention are those compounds of formula (I), hereinafter depicted wherein:

R and $R^1$ each independently represent an alkyl group;

A represents either:

(1) a phenyl group which is optionally substituted, preferably at the 3 and/or 5 position(s), by a halogen atom or a cyano, nitro, trifluoromethyl, carbamoyl, carboxyl, alkoxycarbonyl or alkylsulphonyl group and which may be further substituted by halogen atom(s), alkyl group(s), aryl-containing group(s) having six to twelve carbon atoms, or substituents which form a fused ring thereon; or (2) a heteroaromatic group containing 1 or 2 nitrogen atoms selected from pyrid-3-yl, quinolin-3-yl, isoquinolin-4-yl, pyridazin-4-yl, pyrimidin-5-y1, pyrazin-3-yl, indol-3-yl and thiazol TM 5-yl, optionally substituted by an alkyl or alkoxy group, or a halogen atom; and Y represents:

an ethylene or methylene group or a direct bond; wherein all alkyl groups and moieties, including those in alkoxy, alkoxycarbonyl and alkanoyl groups, can be straight-chain or branched, and, unless otherwise specified, contain one to four carbon atoms;

and stereoisomers and salts thereof.

Particularly important classes of compounds of formula (I) exhibit one of more of the following features:

(i) R and $R^1$ each represent a methyl group;
(ii) A is heteroaromatic and is preferably pyrid-3-yl; and
(iii) Y is a methylene group;

the other symbols being as hereinbefore defined, and their stereoisomers and pharmaceutically acceptable salts.

The presence of an alkoxy group on the ring creates an isomeric center in the molecule which in association with the adjacent asymmetric ring carbon atom leads to 4 stereoisomers which, optionally, can be separated into 2 racemic pairs. The racemic pair and enantiomers in which the —$OR^1$ and —CSNHR groups are in the trans relationship are preferred.

In certain cases the substituents A, R and $R^1$ can also contribute to stereoisomerism. All such forms are also embraced by the present invention.

A particularly important compound of the present invention is:

A  (±)-trans-2-Methoxy-N-methyl-1-(pyrid-3-yl)cyclohexanecarbothioamide as well as its stereoisomeric forms and pharmaceutically acceptable salts thereof.

The letter A is allocated to the compound for ease of reference in other parts of the specification.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; and premature labor.

The compounds also have utility in the inhibition of head hair loss associated with male pattern baldness, by topical application.

For example, compounds of general formula (I) were submitted to:

Vaso-relaxant Activity Test

The test method used was adapted from those described by Winslow et. al. [Eur. J. Pharmacol., 131, 19–228 (1986)] and Karaki [J. Pharmacol. Methods, 18, 1–21 (1987)] for differentiating vaso-relaxant activity.

Activity against contractions included by low $K^+$ concentrations in the isolated rat aorta Thoracic aorta was removed from rats and transverse strips, denuded of endothelium, were suspended in a bath containing Krebs solution. The tension was recorded and a contraction induced by addition of 20 mM $K^+$ (potassium ion) to the bathing solution. The test compound was added to the bath as a solution in increasing cumulative concentration. The concentration in the bathing solution of the test compound which reduced the $K^+$-induced contraction by 90% was determined and, expressed as the effective concentration, had a value of 0.4 μM.

The compounds of general formula (I) can be prepared by the application and adaptation of known methods, for example as hereinafter identified. By the term "known methods" as used in this specification is meant methods heretofore used or described in the literature.

According to a feature of the present invention, compounds of formula (I), as hereinbefore defined, may be prepared by the reaction of a compound of formula (II), wherein A, Y and R are as hereinbefore defined and $P^1$ is a base-stable, acid-labile protecting group, e.g. the 2-methoxyethoxymethyl group, with a compound of formula:

$$R^1-Z \qquad (III)$$

wherein $R^1$ is as hereinbefore defined and Z is a halogen, preferably iodine, atom, in the presence of a base, e.g. an alkali-metal alkoxide such as potassium t-butoxide, in an inert organic solvent, such as tetrahydrofuran, at a temperature from −70° C. to 25° C., followed by acid hydrolysis using, for example, hydrochloric acid.

Compounds of formula (II), wherein A, Y, R and $P^1$ are as hereinbefore defined, may be prepared by the reaction of a compound of formula (IV), wherein A, Y and R are as hereinbefore defined, with a compound of formula:

$$P^1-Z^1 \qquad (V)$$

wherein $P^1$ is as hereinbefore defined and $Z^1$ is a halogen, preferably chlorine, atom, in the presence of a base, e.g. sodium hydride, in an inert organic solvent, e.g. dimethylformamide or tetrahydrofuran or mixtures thereof, at a temperature of from $-10°$ C. to $10°$ C.

The compounds of general formula (IV), wherein A, Y and R are as hereinbefore defined, may be prepared by the reduction of the corresponding compounds of general formula (VI).

The reduction can be carried out in an inert organic solvent such as methanol or dimethylsulphoxide, or a mixture of these solvents at a temperature from $-20°$ C. to $+50°$ C., using an alkali metal borohydride, e.g. sodium borohydride.

Alternatively the reduction can be carried out using an aluminium alkoxide (e.g. the isopropoxide) in an alcoholic solvent (e.g. isopropanol) at temperatures up to reflux.

Both reactions produce both the cis and trans compounds.

Compounds of general formula (VI), wherein A, Y and R are as hereinbefore defined may be prepared by the reaction of a compound of general formula (VII), wherein A and Y are as hereinbefore defined, with an isothiocyanate of the general formula:

$$R-N=C=S \qquad (VIII)$$

wherein R is as hereinbefore defined. The reaction is generally carried out in an anhydrous inert organic solvent such as tetrahydrofuran, dimethylformamide or hexamethylphosphoramide, or a mixture of these solvents, at a temperature from $-80°$ C. to $+50°$ C., in the presence of an inorganic base such as potassium tert.-butoxide, or an organo-lithium derivative such as n-butyllithium, or of sodium hydride.

A stereoselective synthesis of the compounds of formula (VI) may be carried out by reaction of a mixture of enantiomers of general formula (VII) with a chiral auxiliary agent, before being reacted with a compound of general formula (VIII) as hereinbefore described followed by the removal of the chiral auxiliary agent.

The chiral auxiliary agent is typically a compound of formula:

$$Q-NH_2 \qquad (IX)$$

wherein Q is a chiral group, for example asymmetrically substituted pyrollidino or asymmetrically substituted methyl.

Preferred pyrollidines include 1-amino-2-methoxymethyl pyrollidine.

(Asymmetric methyl)amines are preferred reagents.

The preferred (asymmetric methyl)amines have two substituents on the methyl group. Any alkyl substituents may be optionally substituted. All substituents are preferably not alkyl and it is particularly preferred that one is an optionally substituted aromatic or heteroaromatic group. Particularly preferred (asymmetric methyl)amines include 1-phenylethylamine, 1-(1-naphthyl)ethylamine and 1-(pyrid-3-yl)ethyl-amine.

Reaction of a compound of formula (VII) with a compound of formula (IX) produces a compound of formula (X). Reaction of this with a compound of formula (VIII) preferentially produces one enantiomer of compound of formula (XI). The chiral compound of formula (VI) can be produced therefrom by hydrolysis.

Compounds of formula (VII), wherein A is as hereinbefore defined and Y is a methylene or ethylene group, can be made via a dehydrobromination/rearrangement rearrangement reaction of compounds of formula (XII), wherein A is as defined above and $Y^1$ is methylene or ethylene. This may be initiated by a bromide extracting agent such as a silver salt (e.g. silver perchlorate) and carried out in an inert anhydrous solvent (for example an ether such as tetrahydrofuran).

Compounds of formula (XII), wherein A and $Y^1$ are as defined above, can be made by the addition of hypobromous acid across the double bond of compounds of formula (XIII), wherein A and $Y^1$ are as defined above. This may be done by reaction with a brominating agent (e.g. 1,3-dibromo-5,5-dimethylhydantoin) in an aqueous acidic medium, optionally in the presence of a cosolvent.

Compounds of formula (XIII), wherein A and $Y^1$ are as defined above, can be made via a coupling reaction between a phosphorane of formula (XIV) (typically made in situ by the reaction of a compound of formula (XV), wherein $Y^1$ is as defined above and $R^2$ and $Z^2$ are conventional groups present in a Wittig reagent and its phosphonium salt precursor [e.g. phenyl and bromine respectively] with a strong base, such as potassium t-butoxide, in an anhydrous solvent, such as tetrahydrofuran, preferably under an inert atmosphere) and a compound of formula:

$$Z-CHO \qquad (XVI)$$

wherein A is as defined above.

Alternatively compounds of formula (VII), wherein Y is ethylene, methylene or a direct bond and A is as hereinbefore defined, can be made by the removal of methanol from compounds of formula (XVII), wherein A and Y are as defined above. This is typically carried out in the presence of a strongly acidic agent (e.g phosphorus pentoxide or sulphuric acid), optionally in a solvent (such as toluene) and at elevated temperature, followed by hydrolysis of the intermediate enol ether.

Compounds of formula (XVII) can be made by reaction of a compound of formula:

$$A-Z^3 \qquad (XVIII)$$

wherein A is as defined above and $Z^3$ is a halogen, preferably bromine or chlorine atom, in the presence of a strong base, such as an alkyl lithium (e.g. butyllithium), with a compound of formula (XIX), wherein Y is as defined above, in an inert solvent such as an ether (e.g. diethyl ether) or a hydrocarbon (e.g. toluene).

Alternatively, compounds of general formula (VI), wherein A and Y are as hereinbefore defined and R is methyl, can be prepared from compounds of general formula (XX), wherein A and Y are as defined above and $R^3$ is an alkyl group of 1 to 4 carbon atoms or a benzyl or carboxymethyl radical, by reaction with methylamine. The reaction is generally carried out with an excess of amine, without a solvent or in an inert organic solvent such as an ether (e.g. tetrahydrofuran) an aromatic hydrocarbon or an alcohol or a mixture of these solvents at a temperature from room temperature to $130°$ C., optionally under pressure, and the amine may be added in an alcoholic solution, preferably ethanol It may be advantageous for the thiol formed during the reaction to be fixed in the form of a heavy metal salt using a thiol acceptor such as mercuric chloride.

Compounds of formula (XX), wherein Y, A and $R^3$ are as hereinbefore defined may be prepared by the reaction of compounds of formula (VII), wherein Y and A are as hereinbefore defined, with carbon disulphide followed by reaction with a compound of formula:

$$R^3-R^4 \quad \quad (XXI)$$

wherein $R^3$ is as hereinbefore defined and $Z^4$ is halogen, preferably chlorine, bromine or iodine, or a readily displaceable ester group such as methanesulphonyloxy or 4-toluenesulphonyloxy. The reaction is generally carried out in an anhydrous inert organic solvent such as tetrahydrofuran, to which hexamethylphosphoramide may be added, at a temperature from $-80°$ C. to $+50°$ C. in the presence of an organic base such as potassium tert.-butoxide, or an organo-lithium derivative such as butyllithium, or sodium hydride.

Compounds of formulae (III) (V), (VIII), (IX), (XV), (XVI), (XVIII), (XIX) and (XXI) can be made by application or adaptation of known methods or are readily available.

It will be understood that it may be desirable to change one or more of the substituents on the alkyl or aryl groups at an appropriate stage during the synthesis of the compounds of the invention. For example, the compounds of general formula (I) wherein A represents a phenyl group substituted by a carbamoyl group may be alternatively prepared from the corresponding compounds of general formula (I) wherein A represents a phenyl group substituted by a cyano group by the application or adaptation of known methods for such conversion.

It is to be understood that the conversion, for example by known methods, of one compound of general formula (I) into another compound of formula (I) constitutes a feature of the present invention.

By the term "pharmaceutically acceptable salts" as used in this specification is meant salts the anions or cations of which are relatively innocuous to the animal organism when used in therapeutic doses so the the beneficial pharmaceutical properties of the parent compounds of general formula (I) capable of forming salts are not vitiated by side-effects ascribable to those anions or cations.

It is to be understood that, where in this specification reference is made to compounds of formula (I), it is intended to refer also, where the context so permits, to their pharmaceutically acceptable salts.

Suitable acid addition salts for use in pharmaceuticals may by selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

As well as being useful in themselves as active compounds, salts of the compounds of general formula (I) capable of forming salts with acids or bases are useful for the purposes of purification of the parent compounds of general formula (I), for example by exploitation of the solubility differences between the salts and the parent compounds, by techniques well known to those skilled in the art.

The thioformamide derivatives of general formula (I) obtained by the aforedescribed processes can be purified by the usual physical methods, in particular crystallisation and chromatography, especially to resolve mixtures of enantiomers using a chiral column

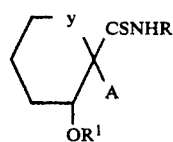
(I)

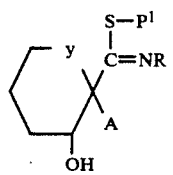
(II)

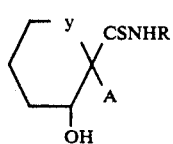
(IV)

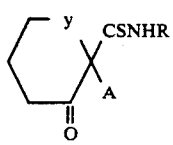
(VI)

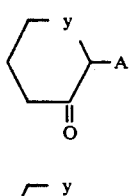
(VII)

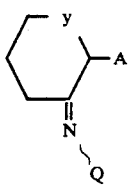
(X)

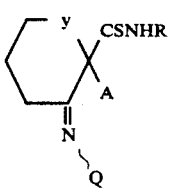
(XI)

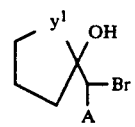
(XII)

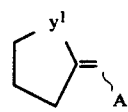
(XIII)

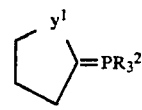 (XIV)

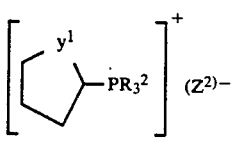 (XV)

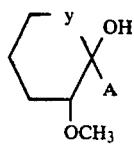 (XVII)

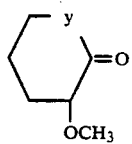 (XIX)

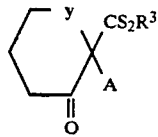 (XX)

EXAMPLES

The following Examples illustrate the preparation of compounds according to the present invention All N.M.R spectra were recorded at 200 MHz. The chemical shifts are expressed in ppm relative to tetramethylsilane. Abbreviations in the text have the following significances:

s=singlet, d=doublet, dd=doublet of doublets, ddd=doublet of doublets of doublets, dt=doublet of triplets, m=multiplet, c=unresolved complex peak, br=broad signal.

EXAMPLE 1

Compound A

A solution of (±)-trans-2-[(2-methoxyethoxymethylthio)(N-methylimino)methyl]-2-(pyrid-3-yl)cyclohexanol (8 g, 23.6 mmol) in tetrahydrofuran (50 ml) at −30° C. was treated with potassium t-butoxide (3.31 g, 29.5 mmol) in one portion. After stirring for 0.5 hours at −30° C. the mixture was cooled to −68° C. and then treated with methyl iodide (2.95 ml, 47.3 mmol) over a period of 0.12 hours. After the addition was complete the temperature was allowed to rise to 25° C. and stirring continued for a further 2 hours. The reaction mixture was poured into water (50 ml) and the resulting mixture was extracted with diethyl ether (3×50 ml). The combined organic extracts were washed with brine (50 ml) and then concentrated in vacuo to one-fifth of the volume (30 ml).

The resulting mixture was treated with hydrochloric acid (1.8 g, 50 mmol) in water (50 ml) and stirred for 2 hours at 25° C. The resulting mixture was neutralized with sodium hydroxide (2 g, 50 mmol) in water (25 ml) and extracted with ethyl acetate (3×50 ml). The combined organic extracts were washed with brine (50 ml) and then dried over magnesium sulphate. Concentration in vacuo afforded a crude oil which was purified by low pressure liquid chromatography, eluting with chloroform methanol (94:6). Recrystallisation from ethyl acetate gave (±)-trans-2-methoxy-N-methyl-1-(pyrid-3-yl)cyclohexanecarbothioamide (0.4 g, 1.51 mmol), m.p. 168°-170° C.;

[N.M.R. (CDCl$_3$): 0.96-1.18 (c, 1H), 1.38-1.79 (c, 4H), 2.10-2.22 (c, 1H), 2.36-2.64 (c, 2H), 3.09 (d, 3H), 3.41 (s, 3H), 3.98-4.07 (m, 1H), 7.25-7.33 (m, 1H), 7.70 (s, 1H), 8.06 (m, 1H), 8.54 (m, 1H), 8.96 (c, 1H)

Found: C, 63.4; H, 7.6; N, 10.5%

Calculated for C$_{14}$H$_{20}$N$_2$OS: C, 63.6; H, 7.63; N, 10.6%].

REFERENCE EXAMPLE 1

A solution of (±)-trans-N-methyl-2-hydroxy--(pyrid-3-yl)cyclohexanecarbothioamide (11.7 g, 46.8 mmol) in a mixture of dimethylformamide (60 ml) and tetrahydrofuran (60 ml) at 20° C. was treated with 50% sodium hydride (2.7 g, 56.2 mmol) over a period of 1 hour. After the addition was complete the mixture was stirred for a further 0.5 hours at 20° C. and then cooled to 5° C. 2-Methoxyethoxymethyl chloride (7.0 g, 56.2 mmol) was then added dropwise over 10 minutes. After 1 hour at 5° C., the reaction mixture was partitioned between diethyl ether (250 ml) and aqueous sodium carbonate solution (2M, 500 ml). The aqueous layer was extracted with diethyl ether (2×250 ml) and the combined organic extracts were successively washed with water (100 ml) and brine (100 ml) and then dried over sodium sulphate. Concentration in vacuo afforded a crude oil (14 g) which was boiled in hexane and treated with decolorizing charcoal (0.5 g). After filtration the solution was concentrated to afford (±)-trans-2-[(2-methoxyethoxymethylthio)(N-methyl-imino)methyl]-2-(pyrid-3-yl)cyclohexanol (11.6 g, 34.3 mmol) as a pale yellow oil;

[N.M.R (CDCl$_3$): 1.30-1.90 (c, 7H), 2.68-2.82 (c, 1H), 3.10-3.21 (c, 1H), 3.30-3.54 (c, 9H), 4.35-4.48 (c, 2H), 4.56 (s, 2H), 7.18-7.28 (m, 1H), 8.12-8.19 (m, 1H), 8.44-8.48 (m, 1H), 8.87-8.91 (c, 1H),

Found: C, 60.7; H, 8.0; N, 8.2%

Calculated for C$_{17}$H$_{26}$N$_2$O$_3$S: C, 60.3; H, 7.7; N, 8.3%].

REFERENCE EXAMPLE 2

A stirred solution of(±)-N-methyl-2-oxo-1-(pyrid-3-yl)cyclohexanecarbothioamide (1.7 g, 6.9 mmol) in methanol (4 ml) at 0° C. was treated with sodium borohydride (262 mg, 6.9 mmol). After 10 minutes at 0° C. the mixture was warmed to 20° C. and a solution formed It was then cooled to 0° C. and stirred for a further 40 minutes. The reaction mixture was then treated with brine (10 ml) and water (30 ml) and extracted with ethyl acetate (2×50 ml). The combined organic extracts were washed with brine (10 ml) then dried over anhydrous sodium sulphate. After concentration in vacuo (30° C.; 14 mmHg) the product was fractionally recrystallized from cyclohexane/ethyl acetate (6:1) (10 ml) to afford (±)-trans-N-methyl-2-hydroxy-1-(pyrid-3-yl)cyclohexanecarbothioamide (1.4 g, 5.6 mmol), m.p. 171°-172° C.;

[N.M.R. (CDCl$_3$): 1.24-2.02 (m, 6H); 2.08-2.28 (dt, 1H), 2.46-2.60 (m, 1H), 3.06-3.12 (d, 3H), 3.54-3.78 (br s, 1H), 4.70-4.86 (m, 1H), 7.26-7.28 (m, 1H), 7.44-7.70 (br, s, 1H), 8.20-8.28 (dt, 1H), 8.48-8.58 (dd, 1H), 8.92-8-96 (d, 1H)

Found: C, 2.3; H, 7.3; N, 11.4; 12.7%

Calculated for $C_{13}H_{18}N_2OS$: C, 62.4; H, 7.3; N, 11.2; S, 12.8%].

The corresponding cis compound could also be isolated from the reaction mixture

REFERENCE EXAMPLE 3

A vigorously stirred solution of (±)-2-(pyrid-3-yl)cyclohexanone (5.5 g, 30 mmol) in anhydrous tetrahydrofuran (50 ml) under argon at −15° C. was treated with potassium t-butoxide (3.36 g, 30 mmol).

After 60 minutes at 0° C., a solution of methyl isothiocyanate (2.4 g, 33 mmol) in anhydrous tetrahydrofuran (10 ml) was added during 5 minutes After 2.5 hours at 0° C. the solution was warmed to 20° C. and then poured into a saturated aqueous brine solution (250 ml). The mixture was extracted with ethyl acetate (50 ml) and then with chloroform (3×50 ml). The combined organic extracts were dried over sodium sulphate and then concentrated in vacuo (30° C.; 14 mmHg).

The crude product was recrystallised from nethanol to give (±)-N-methyl-2-oxo-1-(pyrid-3-yl)-cyclohexanecarbothioamide (4.8 g, 19 mmol), m.p. 88°-190° C.;

[N.M.R. (CDCl$_3$): 1.62-2.06 (m, 4H), 2.42-2.60 (m, 2H), 2.60-2.82 (m, 1H), 2.84-3 06 (m, 1H), 3.16-3.2 (d, 3H), 7.24-7.34 (ddd, 1H), 7.6-7.68 (ddd, 1H), 43-8 47 (d, 1H), 8.48-8.54 (dd, 1H), 8.9-9.2 (br s, 1H)

Found:. C, 62.9; H, 6.6; N, 11.3; S, 13.1%

Calculated for $C_{13}H_{16}N_2OS$: C, 62.9; H, 6.5; N, 11.3; S, 12.9%].

REFERENCE EXAMPLE 4

A solution of (±)-trans-1-[(pyrid-3-yl)-bromomethyl]cyclopentanol (10.24 g, 40 mmol) in anhydrous tetrahydrofuran (500 ml) at 0° C. was treated, dropwise during 30 minutes, with a solution of silver perchlorate (9.9 g, 48 mmol) in anhydrous tetrahydrofuran (50 ml). After 60 minutes at 0° C. the mixture was poured into a mixture of saturated aqueous brine solution (500 ml) and 10% w/v aqueous sodium bicarbonate solution (500 ml). The resulting mixture was filtered and then extracted with ethyl acetate (2×500 ml). The combined organic extracts were washed with brine and then dried over sodium sulphate. Concentration in vacuo (30° C.; 14 mmHg) afforded a crude oil which was recrystallised from cyclohexane (120 ml) to give (±)-2-(pyrid-3-yl)-cyclohexanone (6.7 g, 38 mmol), m.p. 78°-80° C.;

[N.M.R. (CDCl$_3$): 1.72-2.12 (m, 4H), 2.12-2.40 (m, 2H), 2.40-2.64 (m, 2H), 3.56-3.72 (dd, 1H), 7.22-7.32 (m, 1H), 7.44-7.54 (ddd, 1H), 8.34-8.42 (dd, 1H), 8.46-8 54 (dd, 1H)].

REFERENCE EXAMPLE 5

A solution of 3-cyclopentylidenemethylpyridine (62.2 g, 0.39 mol) in acetone (600 ml) and water (100 ml) was treated with a solution of concentrated sulphuric acid (18.9 g, 0.19 mol) in water (100 ml) at 5° C. The ice-cold solution was treated with 1,3-dibromo-5,5-dimethylhydantoin (55 g, 0.19 mol) during 20 minutes. After 3.5 hours at 0° C. the mixture was treated with sodium bicarbonate (33.6 g, 0.4 mol) followed by water (2 l) and then extracted with ethyl acetate (2×500 ml). The organic phase was removed and washed with 10% w/v aqueous sodium bicarbonate solution (500 ml) followed by water (200 ml) and brine (200 ml). The crude extract was dried over sodium sulphate and then filtered through a column of flash silica gel (10 cm×2.4 cm diameter). After concentration in vacuo (20° C.; 14 mmHg) the dark oil crystallized on standing to give (±)-trans-1-[(pyrid-3-yl)bromomethyl]cyclopentanol (56 g, 0.22 mol) m.p. 92°-94° C.; [N.M.R. (CDCl$_3$) 1.36-2.06 (c, 8H), 2.32-2.46(br s, 1H), 5.02 (s, 1H), 7.24-7.34 (ddd, 1H), 8.0-8.1 (ddd, 1H), 8.52-8.56 (dd, 1H), 8.62-8 66 (d, 1H)

Found: C, 51.9; H, 5.6; Br, 30.6; N, 5.5%

Calculated for $C_{11}H_{14}BrNO$: 51.6; H, 5.5; Br, 31.2; N, 5.5%].

REFERENCE EXAMPLE 6

A suspension of cyclopentyltriphenylphosphonium bromide (226 g, 0.55 mol) in anhydrous tetrahydrofuran (1000 ml) at 2° C. was treated with vigorous stirring under an atmosphere of argon, with potassium t-butoxide (61.7 g, 0.55 mol). The dark red mixture was stirred at 5° C. for 80 minutes and then treated with pyridine-3-carbaldehyde (58.9 g, 0.55 mol) during a period of 20 minutes. The reaction mixture was stirred at 0° C. for 2 hours and then at 20° C. for 18 hours. The tetrahydrofuran was removed in vacuo (30° C.; 14 mmHg) and the residue extracted with pentane (2×500 ml). After treatment with decolourising charcoal (5 g), the mixture was filtered through a plug of flash silica gel (Merck 70-230 mesh; 13cm×2 cm diameter) The filtrate was concentrated in vacuo (30° C., 14 mmHg; then 20° C., 0.01 mmHg) to afford 3-cyclopentylidenemethylpyridine (54 g, 0.34 mol) as an orange oil which was used without further purification;

[N.M.R. (CDCl$_3$): 1.6-1.95 (m, 4H), 2.4-2.65 (m, 4H), 6.26-6.34 m, 1H), 7.16-7.25 (ddd, 1H), 7.56-7.65 (ddd, 1H), 8.52-8.52 (d, 1H)].

REFERENCE EXAMPLE 7A

A 4:1 mixture of (±)-cis/trans-2-methoxy-1-(pyrid-3-yl)cyclohexanol (2 g, 10 mmol), toluene and phosphorus pentoxide (3.4 g, 24 mmol) was heated at reflux for 5 hours. The mixture was then filtered and the precipitate partitioned between sodium hydroxide solution (2M, 80 ml) and diethyl ether (25 ml). The aqueous layer was extracted with ether (3×25 ml) and the combined organic extracts were dried over sodium sulphate. Concentration in vacuo afforded a crude oil which was purified by flash chromatography to give 2-(pyrid-3-yl)cyclohexanone (0.7 g, 4 mmol)

REFERENCE EXAMPLE 7B (±)-cis/trans-2-Methoxy-1-(pyrid-3-yl)cyclohexanol (270.6 g) was added dropwise to concentrated sulphuric acid (1.6l). The temperature rose to 40° C. and cold water cooling was used to prevent this being exceeded. The dark red/brown solution was stirred for 6.5 hours as its temperature fell to 28° C.

The solution was added to vigorously stirred ice/water (15l) and the brown mixture stirred for 10 minutes until its temperature had dropped to −5° C.. Aqueous sodium hydroxide (12M, 4.82 l) was added over 30 minutes until the pH reached 5. A further 10l of ice was added during this addition to prevent the temperature rising above 30° C. Sodium carbonate (88 g) was then added portionwise to pH8, followed by sodium chloride (5.3kg).

Diethyl ether (5l) was added and the mixture stirred vigorously. The ether was separated and the aqueous layer extracted with further quantities of diethyl ether (5l+4l+3l+2l). The combined extracts were dried (MgSO$_4$) and evaporated to give a yellow solid. This was triturated with diethyl ether (500 ml) to give 2-(pyrid-3-yl)cyclohexanone 200 g) as a cream solid.

REFERENCE EXAMPLE 8

To a solution of 2.5M n-butyllithium in hexane (13.2 ml, 33 mmol) at −78° C. was added diethyl ether (15 ml) followed by a solution of 3-bromopyridine (4.7 g, 30 mmol) in ether (90 ml) over a period of 10 minutes. After 1 hour at −78° C. a solution of (±)-2-methoxycyclohexanone (3.84 g, 30 mmol) in ether (20 ml) was added dropwise during 10 minutes. After 2 hours at −78° C. and 30 minutes at 0° C. the reaction mixture was warmed to 20° C. and then poured onto ice (150 g). The mixture was extracted with ether (2×50 ml) and then the combined organic extracts were extracted with 1N hydrochloric acid (50 ml). This aqueous extract was washed with ether (20 ml) and then treated with 2M sodium hydroxide solution (25 ml) and extracted with ether (3×100 ml). The organic extracts were combined, washed with brine then dried over anhydrous sodium sulphate Concentration in vacuo afforded (±)-2-methoxy-1-(pyrid-3-yl)cyclohexanol (5.0 g, 24 mmol) as a 4:1 mixture of cis and trans isomers;

[N.M.R. (CDCl$_3$): 1.2–2.14 (c), 2.24–2.44 (m), 2.90–3.28 (c), 3.48–3.60 (m), 7.18–7.30 (m), 7.78–7.96 (m), 8.40–8.48 (m), 8.62–8.72 (m), 8.78–8.82 (m)].

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, inert diluents commonly used in the art such as water and liquid paraffin. Besides inert diluents such compositions may comprise adjuvants, such as wetting, and suspending agents, and sweetening, flavoring, perfuming and preserving agents. The compositions according to the invention for oral administration also include capsules of absorbable material such as gelatin, containing one or more of the active substances with or without the addition of diluents or excipients.

Compositions according to the invention for parenteral administration include sterile aqueous, aqueous-organic, and organic solutions, suspensions and emulsions. Examples of organic solvents or suspending media are propylene glycol, polyethylene glycol, vegetable oils such as olive and injectable organic esters such as ethyl oleate. The compositions may also contain adjuvants such as stabilising, preserving, wetting, emulsifying and dispersing agents. They may be sterilised by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained Obviously, several unit dosage forms may be administered at about the same time. The dose employed will be determined by the physician, and depends upon the desired therapeutic effect, the route of administration, the duration of the treatment and the condition of the patient. In the adult, the doses are generally from 0.001 to 50 mg/kg body weight per day by oral administration. By inhalation, either as a nebulized solution or as a formulated dry powder, the preferred daily dosage is from 0.001 to 5 mg/kg body weight.

The compounds may also be applied topically for inhibition of head hair loss associated with male pattern baldness, the preferred daily dosage being from 0.1 to 10 mg/kg body weight applied, for example, in ml portions two or three times per day.

The following Example illustrates a pharmaceutical composition according to the present invention.

COMPOSITION EXAMPLE

No. 2 size gelatin capsules each containing:

| | |
|---|---|
| (±)-trans-2-Methoxy-N-methyl-1-(pyrid-3-yl)-cyclohexanecarbothioamide | 20 mg |
| Lactose | 100 mg |
| Starch | 60 mg |
| Dextrin | 40 mg |
| Magnesium stearate | 1 mg | were prepared in accordance with the usual procedure.

We claim:

1. A thioformamide derivative of the formula I $$\text{(I)}$$

wherein:
R and R$^1$ each independently represent an alkyl group;
A represent pyrid-3-yl
Y represents:
  an ethylene or methylene group or a direct bond; wherein all alkyl groups can be straight-chain or branched, and, unless otherwise specified, contain one to four carbon atoms;
  or stereoisomers or salts thereof.

2. A compound according to claim 1 which exhibits at least one of the following features:
   (i) R and R$^1$ each represent a methyl group;
   (ii) A is pyrid-3-yl; and
   (iii) Y is a methylene group.

3. A compound according to claim 1 wherein the —OR$^1$ and —CSNHR groups are in the trans configuration.

4. A compound according to claim 1 which is (±)-trans-2-methoxy-N-methyl-1-(pyrid-3-yl)-cyclohexanecarbothioamide or pharmaceutically acceptable salts thereof.

5. A pharmaceutical composition comprising a thioformamide derivative according to claim 1 or a pharmaceutically acceptable salt thereof, in association with a pharmaceutically acceptable carrier or coating.

6. A composition according to claim 5 for use in treatment or therapy of a mammal.

7. The composition according to claim 6, wherein the mammal is man.